(12) United States Patent
Perry et al.

(10) Patent No.: US 8,808,363 B2
(45) Date of Patent: Aug. 19, 2014

(54) VASCULAR PROSTHESIS

(75) Inventors: Michael David Perry, Los Altos, CA (US); Robert G. Matheny, Norcross, GA (US)

(73) Assignee: CorMatrix Cardiovascular, Inc., Roswell, GA (US)

( * ) Notice: Subject to any disclaimer, the term of this patent is extended or adjusted under 35 U.S.C. 154(b) by 74 days.

(21) Appl. No.: 13/573,226

(22) Filed: Aug. 31, 2012

(65) Prior Publication Data

US 2014/0067046 A1   Mar. 6, 2014

(51) Int. Cl.
*A61F 2/06* (2013.01)

(52) U.S. Cl.
USPC ... 623/1.36; 623/1.41; 623/23.72; 623/23.76; 606/232; 606/213

(58) Field of Classification Search
CPC ................ A61B 17/0401; A61B 17/0487
USPC .................. 623/1.36, 1.35; 606/232, 213
See application file for complete search history.

(56) References Cited

U.S. PATENT DOCUMENTS

| | | | |
|---|---|---|---|
| 2006/0217762 A1* | 9/2006 | Maahs et al. | 606/213 |
| 2011/0276091 A1* | 11/2011 | Melanson et al. | 606/232 |
| 2012/0016412 A1* | 1/2012 | Mavani et al. | 606/213 |

* cited by examiner

*Primary Examiner* — Thomas J Sweet
*Assistant Examiner* — Tiffany Shipmon
(74) *Attorney, Agent, or Firm* — Francis Law Group (57) ABSTRACT

A vascular prosthesis comprising a tubular shaped expandable ECM member and at least one anchoring mechanism. In one embodiment, the anchoring mechanism comprises proximal and distal single or dual-ring anchors. In one embodiment, the anchoring mechanism comprises a multiple-ring anchor. The anchors preferably comprise a biodegradable metal, such as magnesium. The anchors can also comprise a shape memory alloy, such as nitinol, and a cross-linked ECM material. In some embodiments, the ECM member includes a pharmacological agent.

13 Claims, 6 Drawing Sheets

VASCULAR PROSTHESIS

FIELD OF THE INVENTION

The present invention relates to methods and apparatus for repairing damaged or diseased vessels. More particularly, the present invention relates to vascular endografts or prostheses employing extracellular matrix materials to treat and/or repair damaged or diseased vessels.

BACKGROUND OF THE INVENTION

As is well known in the art, treatment of various medical conditions commonly involves implantation of medical devices and prostheses into a body. Illustrative is the implantation or deployment of a vascular prosthesis, e.g., endograft or stent device, into a cardiovascular vessel, e.g. vein or artery, to treat and/or repair a diseased or damaged region therein.

As is also well known in the art, vascular prostheses, i.e. stents, are often employed to provide an artificial conduit proximate a diseased or damaged vessel region in and/or maintain an open passageway through a cardiovascular vessel. Such vascular prostheses can be designed for temporary placement, i.e. to maintain the patency of the vessel, or permanent placement.

There are, however, several drawbacks and disadvantages associated with conventional vascular prostheses. A common problem associated with implantable vascular prostheses is intimal hyperplasia after intervention in the vessel, such as a coronary artery. Indeed, it has been found that a significant percentage of arterial bypass grafts and vein grafts fail due to intimal hyperplasia after coronary bypass surgery. Endothelial denudation, platelet adherence, and leukocyte infiltration are some of the functions that can contribute to the proliferation of vascular smooth muscle cells in the vessel and subsequent onset of arterial stenosis.

Further, many conventional vascular prostheses; particularly, stents are often constructed from various polymeric materials, such as poly(ethylene terephthalate) (PET). Such prostheses often cause irritation and undesirable biologic responses from the surrounding tissues in a vessel.

Although conventional vascular prostheses are designed to be implanted for an extended period of time, it is sometimes necessary to remove the device prematurely, for example, because of poor patency or harsh biological responses. In such instances, the device generally must be removed through a secondary surgical procedure, which can, and in many instances will, result in undesirable pain and discomfort to the patient and possibly additional trauma to the vessel tissue. In addition to the pain and discomfort, the patient must be subjected to an additional time consuming and complicated surgical procedure with the attendant risks of surgery.

More recently, bioabsorbable and/or biodegradable prostheses have been developed in an effort to eliminate the harsh biological responses associated with conventional polymeric and metal vascular prostheses. There are, however, several known disadvantages associated with bioabsorbable and biodegradable prostheses.

One major disadvantage is that the bioabsorbable and biodegradable materials and, hence, prostheses often break down at a faster rate than is desirable for the application. A further disadvantage is that the bioabsorbable and biodegradable materials can, and in many instances will, break down into large, rigid fragments that can cause obstructions in the interior of a vessel.

A further disadvantage associated with conventional vascular prostheses is that existing means for securing the prosthesis into or onto biological tissue within a body vessel have had limited success. Often the securing means comprises engaging the prosthesis to the surrounding tissues by physical or mechanical means, such as disclosed in U.S. Pat. No. 7,918,882. Another securing means comprises modifying the prosthesis surface or material to induce the production of fibrous (scar) tissue to anchor the prosthesis upon implantation within the vessel.

There is thus a need to provide improved vascular prostheses that substantially reduce or eliminate (i) intimal hyperplasia after intervention in a vessel, (ii) the harsh biological responses associated with conventional, and (iii) employ effective vessel securing means.

There is also a need to provide vascular prostheses that can replace or improve biological functions or promote the growth of new tissue in a subject.

There is also a need to provide vascular prostheses that substantially reduce or eliminate the formation of inflammation and infection.

There is also the need to provide vascular prostheses having mechanical compatibility or enhanced mechanical properties. As is well known in the art, a mismatch between the stiffness, hardness, and porosity of a prosthesis in comparison to the surrounding tissue environment can cause irritation and other complications after implantation.

It is therefore an object of the present invention to provide vascular prostheses that substantially reduce or eliminate (i) intimal hyperplasia after intervention in a vessel, (ii) the harsh biological responses associated with conventional polymeric and metal prostheses, (iii) employ effective vessel securing means, and (iv) the formation of biofilm, inflammation and infection.

It is another object of the present invention to provide vascular prostheses that can effectively replace or improve biological functions or promote the growth of new tissue in a subject.

It is another object of the present invention to provide vascular prostheses that include effective anchoring means for positioning the prostheses proximate target tissue.

It is another object of the present invention to provide vascular prostheses that can administer one or more pharmacological or therapeutic agents to a subject.

It is another object of the present invention to provide vascular prostheses having optimum mechanical compatibility with vascular structures.

SUMMARY OF THE INVENTION

The present invention is directed to improved vascular prostheses employing extracellular matrix (ECM) materials and methods using same to treat and/or repair the intimal surface of damaged or diseased vessels.

In a preferred embodiment of the invention, the vascular prostheses of the invention (hereinafter "ECM prostheses") include a tubular shaped expandable ECM member that is capable of transitioning from a pre-deployment configuration, wherein the ECM member is capable of being positioned within a vessel, e.g., cardiovascular vessel, to a post-deployment configuration, wherein the ECM member is disposed proximate host tissue of the vessel.

In a preferred embodiment, the ECM member comprises an ECM material. According to the invention, the ECM material can be derived from various mammalian tissue sources including, without limitation, the small intestine, large intestine, stomach, lung, liver, kidney, pancreas, placenta, heart, bladder, prostate, tissue surrounding growing enamel, tissue surrounding growing bone, and any fetal tissue from any mammalian organ.

In some embodiments of the invention, the ECM member includes at least one pharmacological agent, i.e. an agent that is capable of producing a desired biological effect in vivo, e.g., stimulation or suppression of cell division, stimulation or suppression of apoptosis, stimulation or suppression of an immune response, anti-bacterial activity, etc.

In a preferred embodiment of the invention, the prostheses of the invention further include at least one anchoring mechanism. In some embodiments of the invention, the anchoring mechanism comprises an expandable proximal anchor. In some embodiments, the anchoring mechanism comprises an expandable distal anchor.

In some embodiments, the anchoring mechanism comprises expandable proximal and distal anchors. In the noted embodiments, the expandable proximal anchor is disposed proximate the proximal end of the ECM member and the expandable distal anchor is disposed proximate the distal end of the ECM member.

In a embodiment of the invention, the proximal and distal anchors comprise a biocompatible material. In some embodiments, the anchors comprise a biocompatible and biodegradable material.

Thus, in some embodiments, the anchors comprise magnesium.

In some embodiments, the anchors comprise nitinol.

In some embodiments, the anchors comprise stainless steel.

In some embodiments, the anchors comprise a cobalt-chrome nickel alloy.

In some embodiments of the invention, the noted metal anchors include an immunomodulating compound.

In some embodiments, the immunomodulating compound comprises a polysaccharide, including, without limitation, GAGs, dextrans, alginate and chitosan.

In some embodiments, immunomodulating compound comprises a polymeric material, including, without limitation, high molecular weight hyaluronic acid (HMW-HA).

In some embodiments of the invention, the proximal and distal anchors comprise a cross-linked ECM material.

In some embodiments of the invention, the anchors comprise a polymeric material.

In a preferred embodiment of the invention, the proximal and distal anchors are capable of transitioning from a first pre-deployment configuration, wherein the pre-deployment configuration of the ECM member is facilitated (or provided), to a first post-deployment configuration, wherein at least the proximal and distal ends of the ECM member are supported and positioned proximate the wall of a vessel (i.e. host tissue thereof) for a predetermined temporary anchor support period of time.

In a preferred embodiment, the anchor support period of time, wherein the proximal and distal ends of the ECM member are positioned proximate the wall of a vessel by the proximal and distal anchors, is within the process of tissue regeneration.

In a preferred embodiment, the proximal and distal anchors maintain contact of the ECM member against the wall of the vessel wall for the anchor support temporary period of time, whereby blood is restricted from gathering between the member and the vessel wall.

In some embodiments of the invention, the anchor support period of time is within the range of approximately 3-12 months. In some embodiments, the anchor support period of time is within the range of approximately 1-3 months.

In some embodiments of the invention, the proximal and distal anchors completely degrade after the anchor support period of time.

In some embodiments of the invention, degradation of the proximal and distal anchors is controlled, whereby substantially all of the anchor material is absorbed proximate the ECM member. In some embodiments, the anchors are encased in remodeled tissue.

In some embodiments, each anchor comprises a simple single. In some embodiments, each anchor comprises a double or dual-ring.

In some embodiments of the invention, the anchoring mechanism comprises an expandable multiple-ring member or anchor having a plurality of inter-connected rings that are disposed proximate the interior wall of an ECM member.

In some embodiments of the invention, the anchoring mechanism comprises a microneedle anchoring member having a plurality of biodegradable microneedles or barbs that are adapted to maintain contact of the ECM member against the wall of a vascular structure when disposed therein.

In some embodiments, the microneedle anchoring member comprises a biodegradable polymeric material, an ECM material or a pharmacological or active agent (i.e. drug), e.g., Heparin®, Plavix®, etc., or a combination thereof.

In some embodiments, the microneedle anchoring member comprises a biocompatible and bioabsorbable metal, such as magnesium.

In some embodiments, the microneedles comprise drug-eluting members, which facilitate the direct administration of a pharmacological agent or composition to tissue, e.g. host tissue of a vascular structure.

According to the invention, upon deployment of an ECM prosthesis of the invention within a vessel, the ECM member, i.e. material, covers the target intima surface of the vessel, e.g., damaged or diseased region of the vessel, and provides a smooth, non-thrombogenic surface. The ECM material will also induce host tissue proliferation, bioremodeling, including neovascularization, e.g., vasculogenesis, angiogenesis, and intussusception, and regeneration of tissue structures with site-specific structural and functional properties.

In some embodiments of the invention, wherein the ECM member includes a pharmacological agent or the anchoring mechanism comprises a microneedle anchoring member having a plurality of drug-eluting microneedles, a desired biological and/or therapeutic action is also effectuated.

A key advantage of the invention is the provision of improved ECM prostheses that include unique anchor members that temporarily position the ECM members proximate target tissue for a pre-determined period of time within the process of tissue growth, and have controlled degradation characteristics.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "an active" includes two or more such actives and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

DEFINITIONS

The term "vessel", as used herein, means and includes any bodily lumen, canal, conduit, duct or passageway, including, but not limited to, blood vessels, bile ducts, the esophagus, the trachea, the ureter and the urethra. A vessel can comprise an existing lumen, canal, conduit, duct or passageway or a lumen, canal, conduit, duct or passageway created by surgical intervention.

The terms "endograft" and "prosthesis" are used interchangeably herein, and mean and include a structure, device or system that is configured for implantation in a body lumen or vessel, including, without limitation, tubular constructs, grafts, and other similar endoluminal structures.

The term "anchor", as used herein in connection with an endograft, means and includes a temporary structure that is configured and employed to "temporarily" position an "endograft" proximate the tissue of a vessel. As discussed in detail herein, in the case of an ECM endograft or construct, the "anchor" is designed and configured to temporary position the ECM endograft proximate a recipient's tissue for a predetermined period of time, which, in some embodiments, is preferably within the process of new tissue regeneration.

The term "extracellular matrix", as used herein, means a collagen-rich substance that is found in between cells in animal tissue and serves as a structural element in tissues. It typically comprises a complex mixture of polysaccharides and proteins secreted by cells. The extracellular matrix can be isolated and treated in a variety of ways. ECM material can be isolated from small intestine submucosa, stomach submucosa, urinary bladder submucosa, tissue mucosa, dura mater, liver basement membrane, pericardium or other tissues. Following isolation and treatment, it is commonly referred to as extracellular matrix or ECM material.

The terms "pharmacological agent", "pharmaceutical agent", "agent", "active agent", "drug", and "pharmaceutical composition" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like. The active drug that can be delivered includes inorganic and organic compounds.

The terms "pharmacological agent", "pharmaceutical agent", "agent", "active agent", "drug", and "pharmaceutical composition" thus mean and include, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e. the protective tissue response to injury or destruction of tissues, which serves to destroy, dilute, or wall off both the injurious agent and the injured tissues. Anti-inflammatory agents thus include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The terms "active agent formulation", "pharmacological agent formulation" and "agent formulation", are also used interchangeably herein, and mean and include an active agent optionally in combination with one or more pharmaceutically acceptable carriers and/or additional inert ingredients. According to the invention, the formulations can be either in solution or in suspension in the carrier.

The term "therapeutically effective", as used herein, means that the amount of the "pharmacological agent" and/or "active agent formulation" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "prevent" and "preventing" are used interchangeably herein, and mean and include reducing the frequency or severity of a disease or condition. The term does not require an absolute preclusion of the disease or condition. Rather, this term includes decreasing the chance for disease occurrence.

The terms "treat" and "treatment" are used interchangeably herein, and mean and include medical management of a patient with the intent to cure, ameliorate, stabilize, or prevent a disease, pathological condition, or disorder. The terms include "active treatment", i.e. treatment directed specifically toward the improvement of a disease, pathological condition, or disorder, and "causal treatment", i.e. treatment directed toward removal of the cause of the associated disease, pathological condition, or disorder.

The terms "treat" and "treatment" further include "palliative treatment", i.e. treatment designed for the relief of symptoms rather than the curing of the disease, pathological condition, or disorder, "preventative treatment", i.e. treatment directed to minimizing or partially or completely inhibiting the development of the associated disease, pathological condition, or disorder, and "supportive treatment", i.e. treatment employed to supplement another specific therapy directed toward the improvement of the associated disease, pathological condition, or disorder.

As used in this application, the term "distal" shall mean the end or direction of an endograft or component thereof that is furthest from a subject's heart. The term "proximal" shall mean the end or direction of an endograft or component thereof that is closest to a subject's heart.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As discussed above, the present invention is directed to improved vascular endografts or prostheses employing extracellular matrix materials and methods using same to treat and/or repair the intimal surface of damaged or diseased vessels. As will readily be appreciated by one having ordinary skill in the art, the present invention substantially reduces or eliminates the disadvantages and drawbacks associated with prior art methods and apparatus for treating damaged or diseased vascular tissue.

As discussed in detail herein, the ECM prostheses of the invention preferably include a tubular shaped expandable ECM member that is capable of transitioning from a pre-deployment configuration, wherein the ECM member is capable of being positioned within a vessel, e.g., cardiovascular vessel, to a post-deployment configuration, wherein the ECM member is disposed proximate host tissue of the vessel.

According to the invention, the ECM material can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No. 12/707,427; which are incorporated by reference herein in their entirety. The mammalian tissue sources include, without limitation, the small intestine, large intestine, stomach, lung, liver, kidney, pancreas, placenta, heart, bladder, prostate, tissue surrounding growing enamel, tissue surrounding growing bone, and any fetal tissue from any mammalian organ.

As is also well known in the art, the urinary bladder submucosa is an extracellular matrix that has the tunica mucosa (which includes the transitional epithelial layer and the tunica propria), a submucosal layer, 3 layers of muscularis, and the adventitia (a loose connective tissue layer). This general configuration is true also for small intestine submucosa (SIS) and stomach submucosa (SS).

Other tissues, such as the liver and pancreas have extracellular matrix called basement membrane. Basement membrane generally does not demonstrate the kind of tensile strength found in submucosa. However, other useful properties may be opportunistically employed from the extracellular matrices of such tissues as the liver, pancreas, placenta and lung tissues; all of which have either basement membrane for extracellular matrix or interstitial membrane (as with the lung). For example, the pancreatic extracellular membrane supports beta islet cells that are critical to pancreatic function. Also, for example, the liver is one tissue known to be able to regenerate itself and therefore special qualities may be present in the liver basement membrane that help facilitate that process.

The extracellular matrices surrounding developing tooth enamel and developing bone also have particular advantages over other matrices in that they support the growth and differentiation of the hard tissues of bone and enamel.

According to the invention, matrices can be used in whole or in part, so that, for example, an extracellular matrix can contain just the basement membrane (or transitional epithelial layer) with the subadjacent tunica propria, the tunica submucosa, tunica muscularis, and tunica serosa. The extracellular matrix component of the composition can contain any or all of these layers, and thus could conceivably contain only the basement membrane portion, excluding the submucosa. However, generally, and especially since the submucosa is thought to contain and support the active growth factors, cytokines and other proteins necessary for in vivo tissue regeneration, the matrix composition from any given source will contain the active extracellular matrix portions that support cell development and differentiation and tissue regeneration.

For purposes of this invention, the extracellular matrix from any of the mammalian tissue consists of several basically inseparable layers broadly termed extracellular matrix. For example, where it is thought that separating a basement membrane from the submucosa is considered to be very difficult, if not impossible, because the layers are thin and it is not possible to delaminate them from each other, the extracellular matrix from that particular layer will probably necessarily contain some basement membrane with the submucosa.

As stated above, in some embodiments of the invention, the ECM member (or material thereof) includes at least one pharmacological agent or composition, i.e. an agent that is capable of producing a desired biological effect in vivo, such as stimulation or suppression of cell division, stimulation or suppression of apoptosis, stimulation or suppression of an immune response, anti-bacterial activity, etc.

Suitable pharmacological compositions include, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological composition comprises an anti-inflammatory.

In some embodiments of the invention, the pharmacological agent comprises a statin, i.e. a HMG-CoA reductase inhibitor. According to the invention, suitable statins include, without limitation, atorvastatin, cerivastatin, fluvastatin, lovastatin, mevastatin, pitavastatin, pravastatin, rosuvastatin, and simvastatin.

As is well known in the art, statins are a class of drugs that primarily function to lower levels of cholesterol production in the liver. Lower levels of cholesterol are achieved via the statins limiting the production of mevalonate in the cholestrol biosynthetic pathway. Statins competitively inhibit HMG-CoA reductase, which, because the molecules are so similar, results in the statins actually taking the place of the HMG-CoA reductase in the cholesterol biosynthetic pathway and reducing the rate at which the mevalonate is produced, subsequently lowering the rate at which cholesterol is produced in the liver.

As indicated, various types of statins include atorvastatin (LIPITOR®) manufactured by Pfizer, fluvastatin (Lescol®), lovastatin (Mevacor®, Altocor®, Altoprev®), pitavastatin (Livalo®, Pitava®), pravastatin (Pravachol®, Selektine®, Lipostat®), rosuvastatin (Crestor®) and simvastatin (Zocor®, Lipex®). Several actives comprising a combination of a statin and another agent such as ezetimbe/simvastatin (Vytorin®) are also available.

Statins also have numerous additional effects on the vascular wall cells, and cardiovascular system. One specific example of this is thromboxane A2 ($TXA_2$). Statins can aid in the reduction of $TXA_2$, which then lowers the platelet activation in the cardiovascular system.

$TXA_2$ is also known as a vasoconstrictor and is especially important during tissue injury and inflammation due to its impact on platelet activation and aggregation as well as its ability to augment the expression of adhesion molecules and chemokines. This allows statins to aid in the reduction of inflammation by the reduction of $TXA_2$ which results in less vascoconstriction, less platelet activation and aggregation, as well as reduced augmentation of adhesion molecules and chemokines.

Statins further impact vascular wall cells and the cardiovascular system by blocking ras homilog gene family, member A (RhoA) activation. Blocking RhoA activation further impacts numerous systems, such as macrophage growth, tissue plasminogen activators (t-PA), plasminogen activator inhibitor type 1 (PAI-1), smooth muscle cell (SMC) proliferation, nitric oxide (NO) production, endothelins, and angiotensin receptors. When statins block RhoA activation, the resultant impact can be seen in many physiological responses of the cardiovascular system, including vascular inflammation, smooth muscle cell production and size, and vasconstriction inter alia.

Macrophage growth reduced by blocking RhoA activation results in the reduction of matrix metalloprotinases (MMPs) and tissue factors (TF). MMPs are part of a larger family of metalloprotinase enzymes that play on important part in wound healing and inflammation. MMPs are produced by activated neutrophils and macrophages (inflammatory cells).

Statins help to reduce inflammatory factors by lowering macrophage growth, which results in reduced production of MMPs. Lowered MMPs also results in a lowered presence of thrombi as the MMPs attach to ECM present in thrombi or damaged ECM at wound sites. Macrophage growth reduction also results in lowered presence of tissue factor (TF).

TF is a protein necessary for the initiation of thrombin formation. This factor also enables cells to initiate the coagulation cascade. Lowered presence of TF results in lowered presence of thrombi in the cardiovascular system, especially in conjunction with reduced MMPs.

Reduced MMPs and reduced TF also results in increased plaque stability which can help to prevent stroke or myocardial infarction by reducing the probability of a portion of the plaque to break off and become lodged within a smaller vessel. Plaque stability further aids in reduction of atherosclerosis.

Blocking RhoA activation also affects the presence of tissue plasminogen activators (t-PA) and plasminogen activator inhibitor type 1 (PAI-1). T-PA is a protein involved in the breakdown of blood clots, and is found on endothelial cells. As an enzyme it catalyzes the conversion of plasminogen to plasmin, the major enzyme responsible for clot breakdown (fibrinolysis).

PAI-1 is a protein that functions as the principal inhibitor of t-PA. Thus, PAI-1 is the principal inhibitor of fibrinolysis. With t-PA presence raised and PAI-1 diminished from the blocking of RhoA activation caused by statins, a reduced thrombotic effect is realized due to reduced opportunity for fibrin to form the polymeric mesh of a hemostatic plug. The reduced MMPs and TF that result from the use of statins work in concert with the increased t-PA and reduced PAI-1 to further reduce the potential for thrombii.

Blocking RhoA activation also affects the presence of Nitric Oxide (NO) in the cardiovascular system. The endothelium uses NO to signal the surrounding smooth muscles to relax, resulting in vasodialation and increased blood flow. NO contributes to vessel homeostasis by inhibiting vascular smooth muscle contraction and growth, platelet aggregation, and leukocyte adhesion to the endothelium. These factors are what allow NO to aid in the reduction of endothelial dysfunction when modulated in such a way as is typical with the administration of statins. The reduction of leukocyte adhesion is a specific example of how the NO production associated with statins aids in the reduction inflammation desired when coadministered locally with an extracellular matrix.

The administration of statins can affect the presence of endothelins and agiotensin receptors. Endothelins and angiotensin receptors can also be affected by the subsequent blocking of RhoA activation associated with statin administration.

Endothelins are proteins that constrict blood vessels and raise blood pressure. There are three isoforms; ET-1, ET-2, and ET-3, with ET-1 being the isoform primarily affected by statins and RhoA activation blocking. Secretion of ET-1 from the endothelium signals vasoconstriction and influences local cellular growth and survival. ET-1 has been implicated in the development and progression of vascular disorders such as atherosclerosis and hypertension. The decrease in the presence of ET-1 associated with statins and RhoA activation blocking results in decreased vasoconstriction and progression of the aforementioned vascular disorders.

Angiotensin receptors are protein coupled receptors that are responsible for the signal transduction of the vasoconstricting stimulus of the main effector hormone angiotensin II. Angiotensin Receptor II Type I (AT-1) is the angiotensin receptor primarily affected by statin administration and RhoA activation blocking. AT-1 mediates vasocontraction, cardiac hypertrophy, vascular smooth muscle cell proliferation, inter alia. The reduction in AT-1 that accompanies statin administration and RhoA activation blocking results in reduced vasoconstriction in the cardiovascular system.

C-Reactive Proteins (CRP) are also influenced by statin administration. CRP are found in the blood; the levels of which deviate in response to differing levels of inflammation. CRP levels diminish in response to statin administration. This functions as a result of a statin's impact on the reduction of inflammation.

Adhesion molecules are proteins that are located on the cell surface and are involved with inflammation and thrombin formation in vascular endothelial cells. With higher incidence of inflammation comes higher incidence of cell adhesion molecules. A statin functions to reduce the presence of adhesion molecules on the endothelium. This helps to reduce inflammation by removing the attachment mechanism for leukocytes and subsequent plaque buildup, the result being lowered chance for atherosclerosis.

Rac-1 is a protein found in human cells. It plays a central role in endothelial cell migration, tubulogenesis, adhesion, and permeability. The expression of Rac-1 can be affected by the administration of statins, specifically such that Rac-1 is decreased by statins. The decrease in the presence of Rac-1 also results in the decrease of reactive oxygen species (ROS). ROS are chemically reactive molecules that have important roles in cell signaling and homeostasis.

Given the benefits of statins on the cardiovascular system, particulary that of inflammation within the cardiovascular system, Applicant has found great benefit from administration of ECMs to cardiovascular tissue, wherein the ECM is impregnated, coated, covered, or otherwise in contact with statins.

Typical systemic administrations of statins range from 10 mg-80 mg daily. In some instances, the dosage of statins required to reach a therapeutically effective local level can result in various toxicities within different organ systems, such as the liver and musculature. However, due to the direct nature of the administration of statins when incorporated in or provided in contact with an ECM material or composition, therapeutically effective dosages may be much smaller resulting nearly absent systemic toxicities.

For example, the ECM material can include 10 mg of a statin to achieve a higher concentration of the statin within a desired tissue, or 10 ug to achieve a lower concentration of the statin within a desired tissue.

In some embodiments of the invention, the ECM material includes 100 ug-5 mg of a statin. In some embodiments of the invention, the ECM material includes 500 ug-2 mg of a statin.

According to the invention, upon deployment of an ECM prosthesis of the invention within a vessel, the ECM member, i.e. material, covers the target intima surface of the vessel, e.g., damaged or diseased region of the vessel, and provides a smooth, non-thrombogenic surface. The ECM material will also induce host tissue proliferation, bioremodeling, including neovascularization, e.g., vasculogenesis, angiogenesis, and intussusception, and regeneration of tissue structures with site-specific structural and functional properties.

In some embodiments of the invention, wherein the ECM member includes a pharmacological composition or, as discussed in detail below, the anchoring mechanism comprises a microneedle anchoring member having a plurality of drug-eluting microneedles, a desired biological and/or therapeutic action is also effectuated In a preferred embodiment of the invention, the ECM prostheses of the invention further include at least one anchoring mechanism. In some embodiments of the invention, the anchoring mechanism comprises an expandable proximal anchor. In some embodiments, the anchoring mechanism comprises an expandable distal anchor. In some embodiments, the anchoring mechanism comprises expandable proximal and distal anchors.

As defined above and discussed in detail below, the term "anchor", as used herein, means and includes a structure that is configured and employed to temporarily position a structure or member, e.g. an ECM member of the invention, proximate host tissue of a vessel. The function of an "anchor" of the invention is thus to temporarily support and position an ECM member of the invention proximate host tissue of a vessel, i.e. vessel wall.

In a preferred embodiment, the anchors of the invention temporarily support and position an ECM member proximate host tissue of a vessel, and maintain contact therewith, for a predetermined anchor support period of time within the process of tissue regeneration.

Thus, in some embodiments, when an ECM member of the invention is deployed in a vessel, the anchors, e.g. proximal and distal anchors, merely position the ECM member proximate host tissue of the vessel (or vessel wall) long enough to initiate blood vessel growth. Once blood vessels begin to grow into the ECM member and stem cells attach to the surface, an endothelium layer or lining grows across the ECM member and starts to remodel into healthy, native vascular wall cells and, thereby, creating a remodeled, natural vascular wall.

Applicants have found that, in most instances, the ECM member will be completely enclosed in an endothelial lining in a minimum time duration of approximately 3-8 weeks and a maximum time duration of approximately 2-6 months.

In a preferred embodiment of the invention, the anchors of the invention are also completely enclosed in the endothelial lining during tissue remodeling, and remain encased in the endothelial lining for a defined period of time during and post healing.

According to the invention, once the anchors and ECM member are enclosed in the endothelial lining, the ECM material begins to be reabsorbed during the tissue remodeling (or regeneration) process, and the anchors are no longer required for structural support.

Thus, in a preferred embodiment of the invention, after tissue remodeling commences (i.e. blood vessel growth is initiated), the roll or function of the anchors transitions from a positioning and supporting function, wherein the anchors position and support the ECM member proximate the host tissue of the vessel, to a reinforcing function, wherein the anchors merely reinforce the ECM member and/or remodeled tissue during (and after) the tissue regeneration process.

Preferably, the radial force exerted on the ECM member by the anchors is highest at deployment. The radial force then diminishes after approximately eight (8) weeks. Once the anchors are completely embedded in the remodeled tissue, the radial force provided by the anchors is minimal, more preferably, zero.

Depending on the material employed to form the anchors, the anchors could be completely absorbed or remain in place with no continued functional use, i.e. function like a rebar in a matrix.

As stated above, in some embodiments, the anchoring mechanism comprises expandable proximal and distal anchors. As discussed in detail herein, in the noted embodiments, the expandable proximal anchor is disposed proximate the proximal end of the ECM member and the expandable distal anchor is disposed proximate the distal end of the ECM member.

In a preferred embodiment of the invention, the proximal and distal anchors are also capable of transitioning from a first pre-deployment configuration, wherein the pre-deployment configuration of the ECM member is facilitated (or provided), to a first post-deployment configuration, wherein at least the proximal and distal ends of the ECM member are supported and positioned proximate the wall of a vessel (i.e. host tissue thereof) for a predetermined temporary anchor support period of time.

In some embodiments of the invention, the proximal and distal anchors preferably comprise a biocompatible material. In some embodiments, the anchors preferably comprise a biocompatible and biodegradable material.

Thus, in some embodiments, the anchors comprise magnesium.

In some embodiments, the anchors comprise nitinol.

In some embodiments, the anchors comprise stainless steel.

In some embodiments, the anchors comprise a cobalt-chrome nickel alloy.

In some embodiments of the invention, the noted metal anchors include a coating of an immunomodulating compound that suppresses acute immune responses, while up regulating chronic immune response (i.e. tissue reconstruction).

In some embodiments, the immunomodulating compound comprises a polysaccharide, including, without limitation, GAGs, dextrans, alginate and chitosan.

In some embodiments, immunomodulating compound comprises a polymeric material, including, without limitation, high molecular weight hyaluronic acid (HMW-HA).

In some embodiments of the invention, the anchors comprise a polymeric material.

In some embodiments of the invention, the anchors comprise a cross-linked ECM material, since the anchors are not required to add vascular structure.

In some embodiments, each anchor comprises a simple single. In some embodiments, each anchor comprises a double or dual-ring.

In some embodiments of the invention, the anchoring mechanism comprises an expandable multiple-ring anchor having a plurality of inter-connected rings that are disposed proximate the interior wall of an ECM member.

In some embodiments of the invention, the anchoring mechanism comprises (or includes) a microneedle anchoring member having a plurality of biodegradable microneedles or barbs that are adapted to maintain contact of the ECM endograft against the wall of a vascular structure when disposed therein.

In some embodiments, the microneedles comprise drug-eluting members that facilitate the direct administration of a pharmacological agent to host tissue, e.g. host tissue of a vascular structure.

Figure 1:
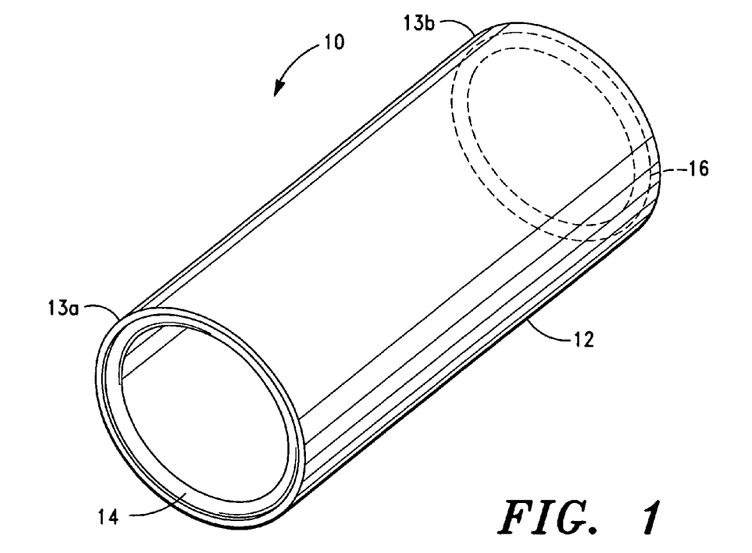
FIG. 1 is a perspective view of one embodiment of an ECM prosthesis, in accordance with the invention.
Figure 2:
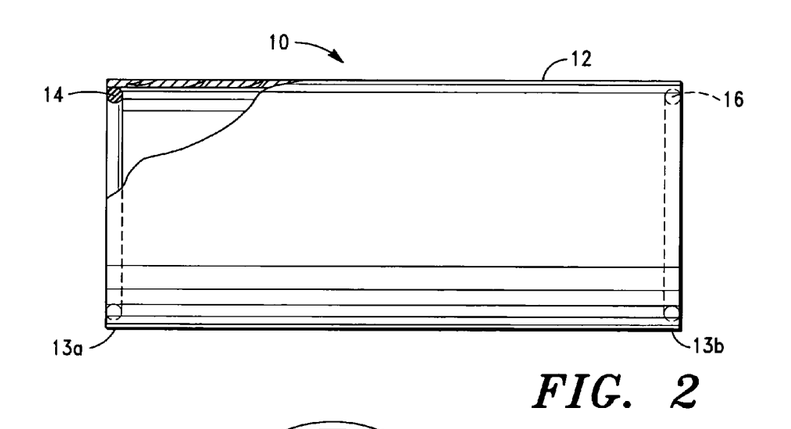
FIG. 2 is a side plan view of the ECM prosthesis shown in FIG. 1, in accordance with the invention.
Figure 3:
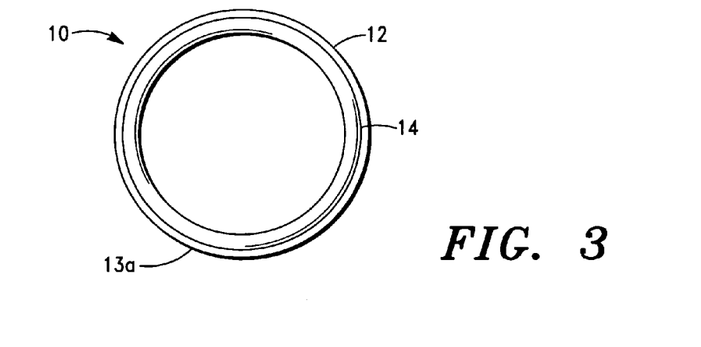
FIG. 3 is a front (or end) plan view of the ECM prosthesis shown in FIG. 1, in accordance with the invention.

Referring now to FIGS. 1-3, there is shown one embodiment of a vascular prosthesis 10 of the invention. As illustrated in FIG. 1, the prosthesis 10 includes a tubular shaped expandable ECM member 12 that is capable of transitioning from a pre-deployment configuration, wherein the ECM member 12 is capable of being positioned within a vessel, e.g., cardiovascular vessel, to a post-deployment configuration, wherein the ECM member 12 is disposed proximate host tissue of the vessel.

In some embodiments of the invention, the ECM member 12 comprises a single layer of ECM material. In some embodiments, the ECM member 12 comprises multiple, preferably wrapped, layers of ECM material.

As stated above, according to the invention, the ECM material can be derived from various mammalian tissue sources including, without limitation, the small intestine, large intestine, stomach, lung, liver, kidney, pancreas, placenta, heart, bladder, prostate, tissue surrounding growing enamel, tissue surrounding growing bone, and any fetal tissue from any mammalian organ.

As set forth above, in a preferred embodiment, the ECM prostheses of the invention further include at least one anchoring mechanism. In some embodiments of the invention, the anchoring mechanism comprises a proximal anchor. In some embodiments of the invention, the anchoring mechanism comprises a distal anchor.

Referring now to FIG. 1, in some embodiments of the invention, the anchoring mechanism comprises expandable proximal 14 and distal 16 anchors. As illustrated in FIG. 1, the proximal 14 and distal 16 anchors comprise single ring members.

In some embodiments of the invention, the anchors 14, 16 (or rings) preferably have a thickness in the range of approximately 0.25-1.0 mm. In some embodiments, the anchors 14, 16 preferably have a thickness in the range of approximately 0.05-0.25 mm.

In some embodiments of the invention, the anchors 14, 16 preferably exert a supporting force on the ECM member ends in the range of approximately 0.5-2 atm when in a post-deployment configuration. In some embodiments, the anchors 14, 16 preferably exert a supporting force of the ECM member ends in the range of 0.05-0.5 atm when in a post-deployment configuration.

As stated above, in some embodiments, the proximal 14 and distal 16 anchors comprise magnesium.

In some embodiments, the anchors 14, 16 comprise stainless steel.

In some embodiments of the invention, the anchors 14, 16 comprise a biocompatible shape memory alloy, including, without limitation, nitinol.

In some embodiments, the anchors 14, 16 comprise a cobalt-chrome nickel alloy.

As also stated above, in some embodiments of the invention, the anchors 14, 16 include a coating of an immunomodulating compound that suppresses acute immune responses, while up-regulating chronic immune response (i.e. tissue reconstruction).

In some embodiments, the immunomodulating compound comprises a polysaccharide, including, without limitation, GAGs, dextrans, alginate and chitosan.

In some embodiments, immunomodulating compound comprises a polymeric material, including, without limitation, high molecular weight hyaluronic acid (HMW-HA).

In some embodiments of the invention, the anchors 14, 16 comprise a polymeric material, more preferably, a biocompatible and biodegradable polymeric material, such as, without limitation, polyesters, poly(amino acids), polyanhydrides, polyorthoesters, polyurethanes, polycarbonates, homopolymers and copolymers of poly(lactic acid) and poly (glycolic acid), copolyesters of e-caprolactone, trimethylene carbonate, and para-dioxanone, and like polymeric materials.

According to the invention, the anchors 14, 16 can also comprise a cross-linked ECM material, since the anchors 14, 16 are not required to add vascular structure.

As illustrated in FIGS. 2 and 3, the anchors 14, 16 are disposed proximate to, more preferably, attached to the ECM member ends 13a, 13b.

According to the invention, the anchors 14, 16 can be attached to the ECM member ends 13a, 13b by various means. Accordingly, in some embodiments of the invention, the anchors 14, 16 are stitched to the ECM member ends 13a, 13b. In some embodiments, the stitches comprise ECM stitches.

In some embodiments of the invention, each anchor 14, 16 is encapsulated in an ECM pocket, e.g., folded over tubular structure ends 13a, 13b.

In a preferred embodiment of the invention, the anchors 14, 16 are capable of transitioning from a first pre-deployment configuration, wherein the pre-deployment configuration of the ECM member is facilitated (or provided), to a first post-deployment configuration, wherein at least the proximal and distal ends 13a, 13b of the ECM member 12 are supported and positioned proximate the wall of a vessel (i.e. host tissue thereof) for a predetermined temporary anchor support period of time.

As stated, the primary function of the anchors 14, 16 (and anchors 22, 24 and 30, discussed below) is to "temporarily" position an ECM member 12 proximate host tissue of a vessel.

In a preferred embodiment, the anchors 14, 16 maintain contact of the ECM member 12 against the vessel wall for the anchor support temporary period of time, whereby blood is restricted from gathering between the member 12 and the vessel wall.

In a preferred embodiment of the invention, the anchors 14, 16 (and anchors 22, 24 and 30) temporarily support and position an ECM member proximate host tissue of a vessel, and maintain contact therewith, for a predetermined anchor support period of time within the process of tissue regeneration.

In some embodiments of the invention, the predetermined anchor support period of time is thus within the range of approximately 12-36 months. In some embodiments, the anchor support period of time is within the range of approximately 3-12 months. In some embodiments, the anchor support period of time is within the range of approximately 1-3 months.

In some embodiments of the invention, the anchors 14, 16 (and anchors 22, 24 and 30) completely degrade after the anchor support period of time.

In some embodiments of the invention, degradation of the anchors 14, 16 (and anchors 22, 24 and 30) is further controlled, whereby substantially all of the anchor material is absorbed proximate the ECM member 12. According to the invention, the noted controlled degradation is achieved by the defined ring thicknesses and supporting forces exerted on the ECM member 12 by the anchors, and the remodeling characteristics effectuated by the ECM member 12 (or material thereof), whereby, when an ECM prosthesis of the invention is deployed in a vessel, i.e. the ECM member 12 and anchors 14, 16 (or anchors 22, 24 or 30) are in a post-deployment configuration), new tissue is generated and encases the anchors. The anchor material is then absorbed while encased by the new tissue, which substantially reduces or eliminates the possibility of the anchor fragments flowing into and obstructing a vessel.

As stated above, in some embodiments of the invention, degradation of the anchors 14, 16 (and anchors 22, 24 and 30) is controlled, whereby the anchors 14, 16 (and anchors 22, 24 and 30) are encased (or enclosed in) an endothelial lining after tissue remodeling commences for a defined period of time during and post healing, which similarly substantially reduces or eliminates the possibility of the anchor fragments flowing into and obstructing a vessel.

Figure 4:
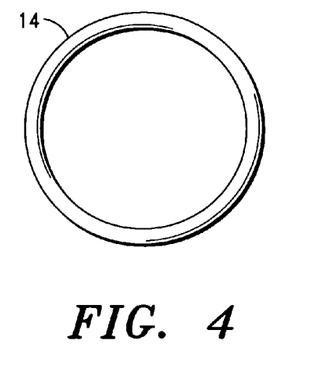
FIG. 4 is a front plan view of one embodiment of a single-ring ECM member anchor, in accordance with the invention.

As illustrated in FIG. 4 (and shown in FIG. 3), each anchor or ring 14, 16 preferably has a substantially circular "post-deployment" configuration or shape, i.e. shape after placement in a vessel. To facilitate deployment of an ECM prosthesis of the invention into a vessel, each anchor 14, 16 also has a predetermined initial or "pre-deployment" configuration or shape.

Figure 5:
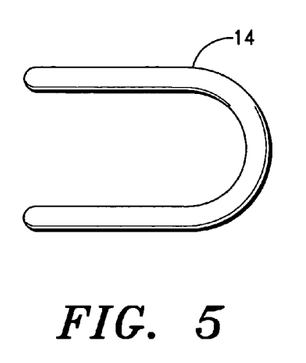
FIG. 5 is a side plan view of the single-ring anchor shown in FIG. 4 in a pre-deployment configuration, in accordance with the invention.
Figure 6:
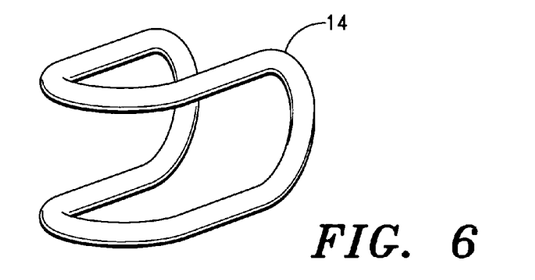
FIG. 6 is a perspective view of the single-ring anchor shown in FIG. 4 in a pre-deployment configuration, in accordance with the invention.

As discussed in detail below, the initial or pre-deployment configuration is dependent upon the anchor material. Thus, in some embodiments of the invention, each anchor 14, 16 is formed with a pre-deployment configuration, such as shown in FIGS. 5 and 6.

In some embodiments of the invention, each anchor 14, 16 is formed with a substantially circular shape, such as shown in FIG. 4. The anchors 14, 16 are then re-configured (via mechanical force means) to achieve the pre-deployment configuration shown in FIGS. 5 and 6.

As indicated above, in some embodiments of the invention, the anchors or rings 14, 16 comprise a biocompatible metal, including, without limitation, stainless steel and magnesium. The metal can also comprise a cobalt-chrome-nickel alloy.

Figure 7:
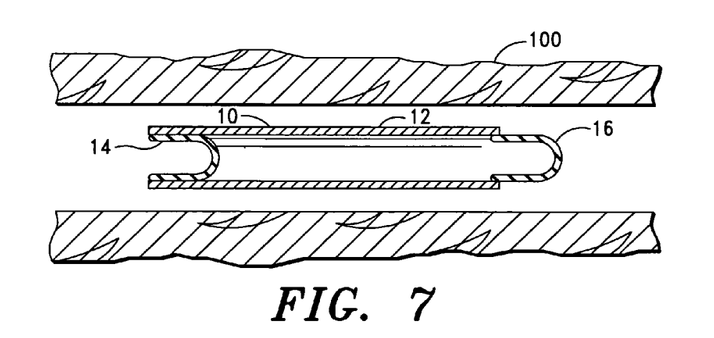
FIG. 7 is a side plan, sectional view of the ECM prosthesis shown in FIG. 1 in a pre-deployment configuration in a cardiovascular vessel, in accordance with the invention.

In these embodiments, the anchors 14, 16 are initially formed in a pre-deployment configuration. In a preferred embodiment of the invention, the pre-deployment configuration similarly comprises a substantially saddle shape, such as shown in FIGS. 5 and 6. As illustrated in FIG. 7, the noted shape reduces the effective diameter of the ECM member 12, i.e. places the ECM member 12 is a pre-deployment configuration, which allows the ECM prosthesis 10 to be easily placed in a vessel 100.

Figure 8:
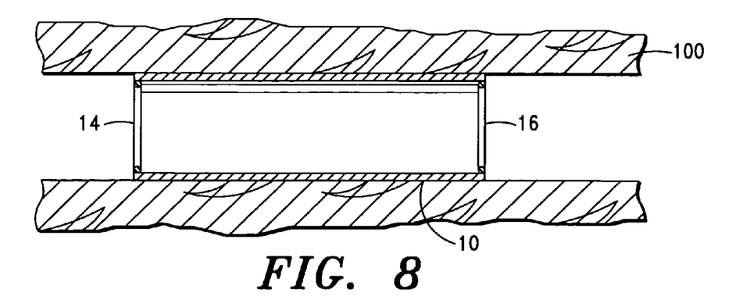
FIG. 8 is a side plan, sectional view of the ECM prosthesis shown in FIG. 1 in a post-deployment configuration in a cardiovascular vessel, in accordance with the invention.

After the ECM prosthesis 10 is placed at a desired position within the vessel 100, the ECM prosthesis 10 is expanded, e.g. via a balloon, whereby the anchors 14, 16 are plastically deformed (i.e. re-configured or expanded) to achieve a substantially circular (and permanent) shape (see FIG. 8), and whereby the anchors 14, 16 temporarily position the ECM member 12, and, hence, prosthesis 10 proximate host tissue of the vessel.

In some embodiments of the invention, the anchors or rings 14, 16 comprise a biocompatible shape memory alloy, including, without limitation, nitinol. In these embodiments, the anchors 14, 16 are initially formed in a substantially circular pre-deployment configuration or shape and subsequently heat-treated at a first temperature (i.e. shape set heat treatment).

The anchors 14, 16 are then deformed or formed in a pre-deployment configuration or shape. In a preferred embodiment of the invention, the pre-deployment configuration or shape comprises a substantially saddle shape, such as shown in FIGS. 5 and 6.

After the ECM prosthesis 10 is placed at a desired position within the vessel 100, the anchors 14, 16 transition to an austenitic phase (i.e. the temperature of the anchors 14, 16 reach and exceed the Nitinol® transition temperature by virtue of the body temperature) and recover (or expand to) their original circular shape, whereby the anchors 14, 16 temporarily position the ECM member 12, and, hence, prosthesis 10 proximate host tissue of the vessel.

Figure 9:
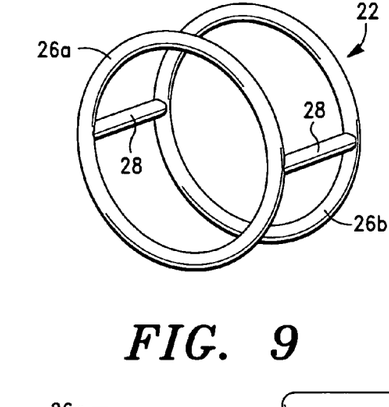
FIG. 9 is a perspective view of one embodiment of a dual-ring ECM member anchor, in accordance with the invention.

In some embodiments of the invention, the anchors of the invention comprise expandable dual-ring members or structures. Referring now to FIG. 9, there is shown one embodiment of an expandable dual-ring anchor 22.

As illustrated in FIG. 9, the anchor 22 includes first and second rings 26a, 26b and at least two connecting links 28. In a preferred embodiment, the rings 26a, 26b are oriented in substantially parallel planes.

In some embodiments of the invention, the rings 26a, 26b similarly have a thickness in the range of approximately 0.25-1.0 mm. In some embodiments, the rings 26a, 26b have a thickness in the range of approximately 0.05-0.25 mm.

In some embodiments of the invention, the connecting links 28 are also disposed on substantially coincident planes, and preferably spaced approximately 180° apart.

In some embodiments of the invention, the anchor includes four (4) connecting links 28, which are similarly disposed on substantially coincident planes. In some embodiments, the links 28 are placed or spaced approximately 90° apart.

Figure 12:
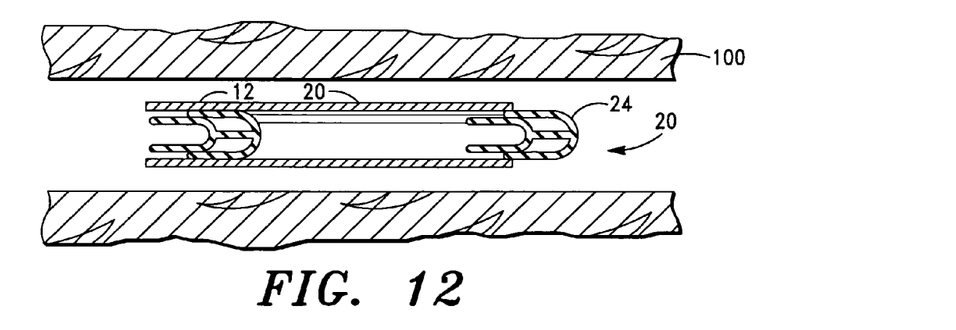
FIG. 12 is a side plan, sectional view of one embodiment of an ECM prosthesis having the dual-ring anchor shown in FIG. 9 in a pre-deployment configuration in a cardiovascular vessel, in accordance with the invention.
Figure 13:
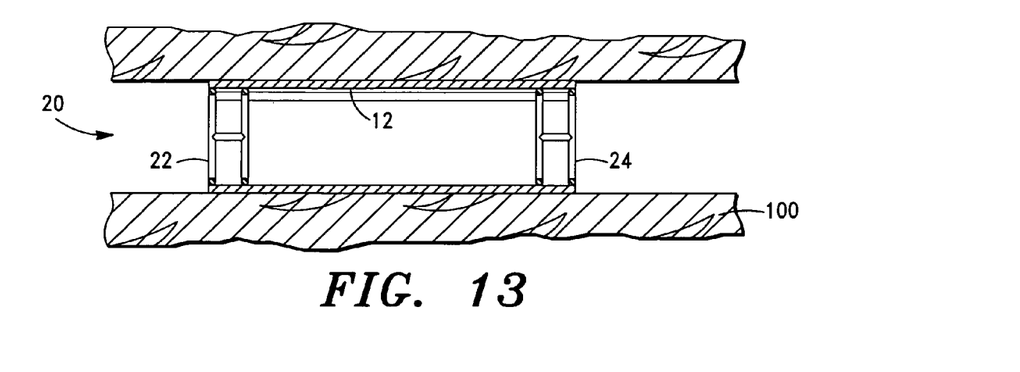
FIG. 13 is a side plan, sectional view of the ECM prosthesis shown in FIG. 12 in a post-deployment configuration in a cardiovascular vessel, in accordance with the invention.

Referring to FIGS. 12 and 13, in one embodiment of the invention, anchor 22 is disposed proximate the proximal end 13a of the ECM member 12 (hereinafter "proximal anchor 22") and an identical dual-ring anchor (denoted "24") is disposed proximate the distal end 13b of the ECM member 12 (hereinafter "distal anchor 24").

In a preferred embodiment of the invention, the anchors 22, 24 are similarly capable of transitioning from a first pre-deployment configuration, wherein the pre-deployment configuration of the ECM member 12 is facilitated, to a post-deployment configuration, wherein at least the proximal and distal ends 13a, 13b of the ECM member 12 are supported and positioned proximate the wall of a vessel (i.e. host tissue thereof) for a predetermined temporary anchor support period of time.

In some embodiments of the invention, the anchors 22, 24 similarly exert a supporting force on the ECM member ends 13a, 13b in the range of approximately 0.5-2 atm when in a post-deployment configuration. In some embodiments, the anchors 22, 24 preferably exert a supporting force of the ECM member ends 13a, 13b in the range of approximately 0.05-0.5 atm when in a post-deployment configuration.

Figure 11:
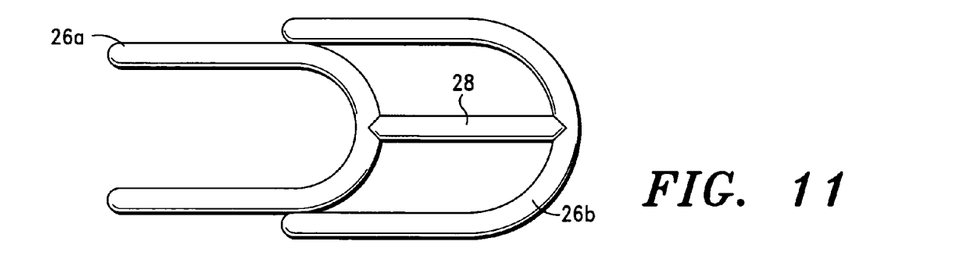
FIG. 11 is a side plan view of the dual-ring anchor shown in FIG. 9 in a pre-deployment configuration, in accordance with the invention.

Referring now to FIG. 11, each anchor ring 26a, 26b similarly has a substantially circular post-deployment configuration. As illustrated in FIG. 12, to facilitate deployment of an ECM prosthesis of the invention into a vessel, each anchor ring 26a, 26b similarly has a predetermined initial or pre-deployment configuration or shape.

In some embodiments, each anchor ring 26a, 26b is similarly formed with a substantially circular shape, such as shown in FIG. 9. The rings 26a, 26b, and, hence, anchors 22, 24 are then similarly re-configured via mechanical force means.

According to the invention, the anchors 22, 24 can similarly comprise a biocompatible metal, including, without limitation, magnesium. The anchors 22, 24 can also comprise stainless steel or a cobalt-chrome-nickel alloy.

Figure 10:
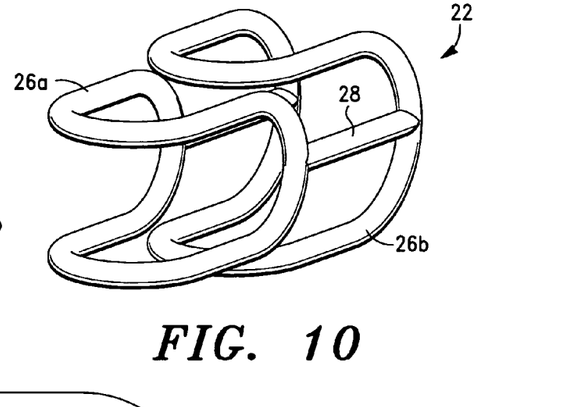
FIG. 10 is a perspective view of the dual-ring anchor shown in FIG. 9 in a pre-deployment configuration, in accordance with the invention.

In these embodiments, the rings 26a, 26b are initially formed in a pre-deployment configuration. In a preferred embodiment of the invention, the pre-deployment configuration similarly comprises a substantially saddle shape, such as shown in FIGS. 10 and 11. As illustrated in FIG. 12, the noted configuration also reduces the effective diameter of the ECM member 12, i.e. places the ECM member is a pre-deployment configuration, which allows the ECM prosthesis 20 to be easily placed in a vessel 100.

After the ECM prosthesis 12 is placed at a desired position within the vessel 100, the ECM prosthesis 20 is similarly expanded, e.g. via a balloon, whereby the anchors 22, 24 are plastically deformed, i.e. expanded, to achieve a substantially circular (and permanent) shape (see FIG. 13), and whereby the anchors 22, 24 temporarily position the ECM member 12, and, hence, prosthesis 20 proximate host tissue of the vessel.

According to the invention, the anchors 22, 24 can similarly comprise a biocompatible shape memory alloy, including, without limitation, nitinol. As discussed above, in these embodiments, the anchors 22, 24 are initially formed in a substantially circular pre-deployment configuration and thereafter mechanically deformed to a saddle shape, such as shown in FIGS. 10 and 11. After deployment of the ECM prosthesis 20 into a body lumen or vessel, the rings 26a, 26b recover (or expand to) their original circular shape, whereby the anchors 22, 24 similarly temporarily position the ECM member 12, and, hence, prosthesis 20 proximate host tissue of the vessel.

As indicated above, in some embodiments of the invention, the anchoring mechanism comprises an expandable multiple-ring anchor having a plurality of inter-connected rings that are disposed proximate the interior wall of the ECM member. In some embodiments of the invention, one or more of the rings are not connected, e.g. a plurality of single ring anchors, as shown in FIG. 1.

Figure 14:
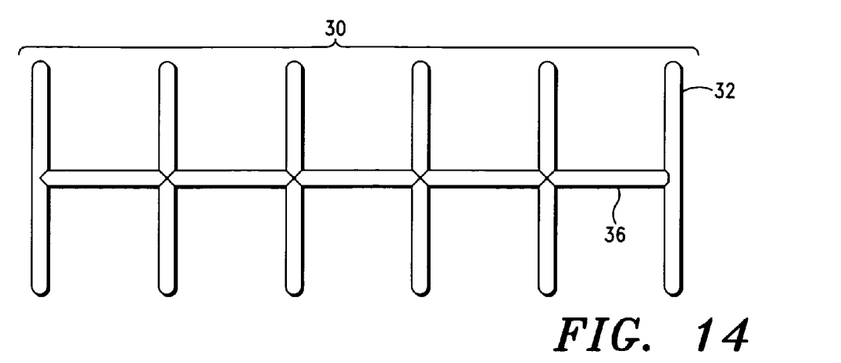
FIG. 14 is a side plan view of one embodiment of a multi-ring anchor, in accordance with the invention.

Referring now to FIGS. 14-17, there is shown one embodiment of multi-ring anchor 30 of the invention. As illustrated in FIG. 14, the multi-ring anchor 30 includes rings 32 and connecting links 36. According to the invention, the anchor 30 can comprise any number of rings 32 and connecting links, e.g., 4, 6 or 7 rings 32.

In some embodiments of the invention, the rings 32 similarly have a thickness in the range of approximately 0.25-1.0 mm. In some embodiments, the rings 32 have a thickness in the range of approximately 0.05-0.25 mm.

According to the invention, the anchor 30 is similarly capable of transitioning from a pre-deployment configuration, wherein the pre-deployment configuration of the ECM member 12 is facilitated, to a post-deployment configuration, wherein the ECM member 12 is supported and positioned proximate the wall of a vessel (i.e. host tissue thereof) for a predetermined temporary anchor support period of time.

According to the invention, each anchor ring 32 can similarly comprise any of the aforementioned materials.

Preferably, each anchor ring 32 similarly has a substantially circular post-deployment configuration.

Figure 15:
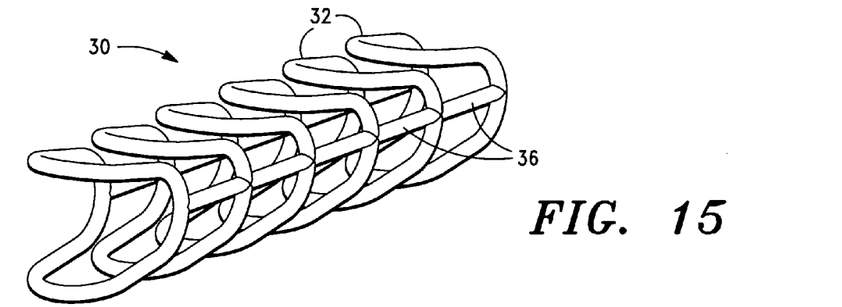
FIG. 15 is a perspective view of the multi-ring anchor shown in FIG. 14 in a pre-deployment configuration, in accordance with the invention.
Figure 16:
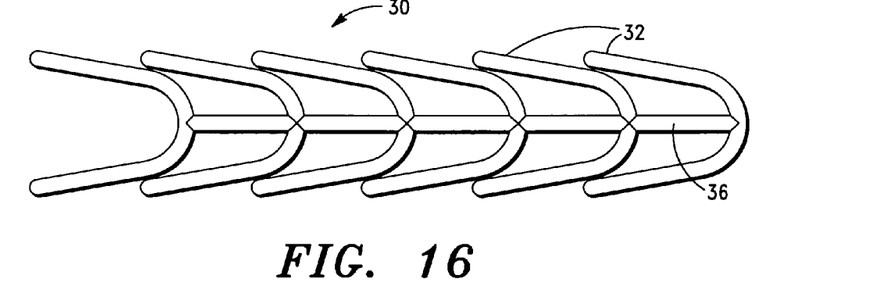
FIG. 16 is a side plan view of the multi-ring anchor shown in FIG. 14 in a pre-deployment configuration, in accordance with the invention.

As illustrated in FIGS. 15-16, to facilitate deployment of an ECM prosthesis of the invention into a vessel, each anchor ring 32 similarly has a predetermined initial or pre-deployment configuration or shape. The pre-deployment configuration or shape is similarly dependent upon the material employed to form the rings 32.

Figure 17:
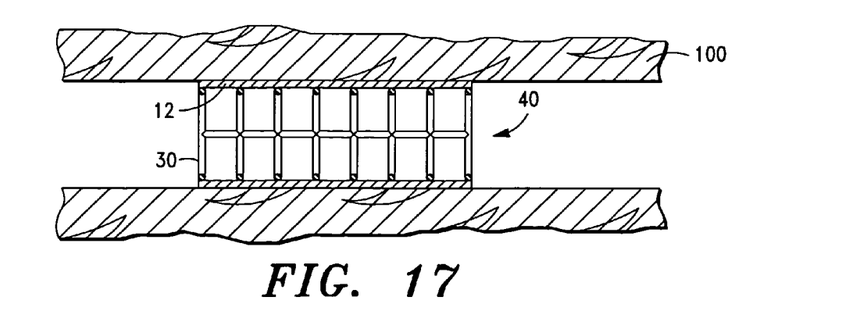
FIG. 17 is a side plan, sectional view of one embodiment of an ECM prosthesis having the multi-ring anchor shown in FIG. 14 in a post-deployment configuration in a cardiovascular vessel, in accordance with the invention.

Depending upon the anchor ring material, each ring 32 preferably achieves a post-deployment shape within a vessel 100, such as shown in FIG. 17, by the aforementioned means, whereby the anchor 30 temporarily positions the ECM member 12, and, hence, prosthesis 40 proximate host tissue of a vessel.

A significant advantage of the multi-ring anchor 30 is that the anchor 30 can support a much longer span inside of the ECM member 12 with optima support using multiple rings 32 with the same separation distance, or varied for optimal support with multiple anchors, or one anchor the complete length of the ECM member 12, and, hence, prosthesis 40.

In some embodiments of the invention, the anchoring mechanism includes a microneedle anchoring member having plurality of biodegradable microneedles or barbs that are adapted to maintain contact of the ECM member, e.g., member 12, against the wall of a vascular structure when disposed therein.

Suitable microneedle anchoring members are disclosed in Co-Pending application Ser. No. 13/686,131, filed on Nov. 27, 2012; which is incorporated by reference herein in its entirety According to the invention, various shaped microneedles or barbs can be employed within the scope of the invention; provided, the microneedle or barb has a head (or head region) that is able to pierce tissue and remain engaged to the tissue for a predetermined period of time.

In some embodiments, the microneedle anchoring member and, hence, microneedles comprise a biodegradable polymeric material, an ECM material or a pharmacological agent or composition (i.e. drug), e.g., Heparin®, Plavix®, etc., or a combination thereof.

In some embodiments, the microneedle anchoring member and, hence, microneedles comprise a biocompatible and bioabsorbable metal, such as magnesium.

In some embodiments, the microneedles comprise drug-eluting members that facilitate the direct administration of a pharmacological agent or composition to host tissue.

In some embodiments of the invention, the drug-eluting capability is facilitated by forming at least one, more preferably, each microneedle out of a pharmaceutical composition, whereby upon engagement of the biodegradable microneedles to a recipient's tissue, the microneedles dissolve or degrade and the pharmaceutical composition is administered to the recipient at the engagement site.

In some embodiments, the drug-eluting capability is facilitated by coating at least one, more preferably, each microneedle with a pharmaceutical composition, whereby upon engagement of the microneedles to a recipient's tissue, the pharmaceutical composition is absorbed and, hence, administered to the recipient.

In some embodiments of the invention, at least one, more preferably, each microneedle has an internal reservoir that is adapted to receive and contain a pharmaceutical composition therein. According to the invention, upon engagement of the biodegradable microneedles to a recipient's tissue, the microneedles dissolve or degrade and the pharmaceutical composition contained in the reservoir is administered to the recipient.

In some embodiments of the invention, the microneedle has an internal reservoir that is adapted to receive and contain a pharmaceutical composition therein and at least one, more preferably, a plurality of lumens in communication with the reservoir and, hence, pharmaceutical composition contained therein. The microneedle also includes a biodegradable or bioabsorbable coating (or sealing layer) on the outer surface to temporarily seal reservoir and inter-connected lumens. Upon engagement of the microneedles to a recipient's tissue, the coating dissolves or degrades and the pharmaceutical composition contained in the reservoir is administered to the recipient via the microneedle lumens.

As set forth in detail in Co-Pending application Ser. No. 13/686,131, the on-set and rate of administration of a pharmacological composition can be determined and regulated by, among other things, the composition and/or properties of the base microneedle, e.g. dissolution rate, size of lumens, etc., and the composition and/or properties of the pharmacological and sealing coatings.

Figure 18:
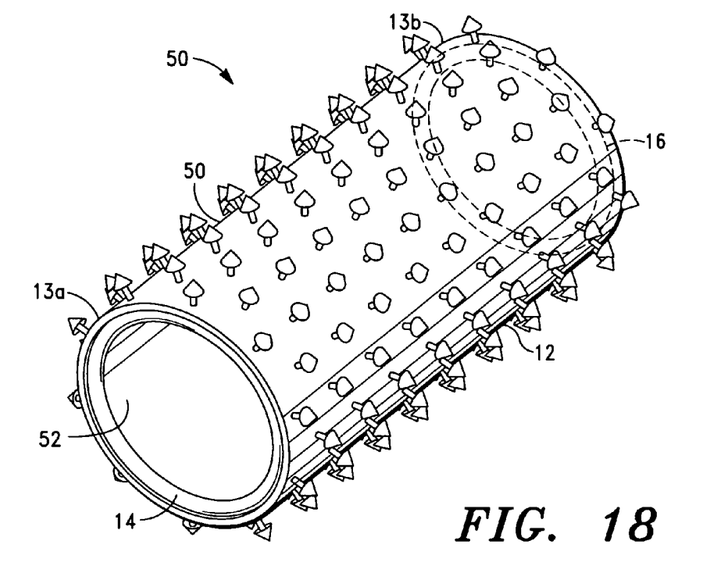
FIG. 18 is a perspective view of one embodiment of an ECM prosthesis having the single-ring anchor shown in FIG. 9 and a microneedle member, in accordance with the invention.
Figure 19:
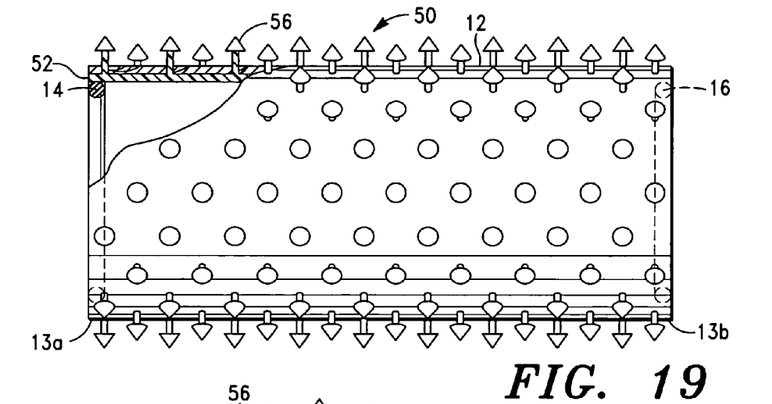
FIG. 19 is a side plan, partial sectional view of the ECM prosthesis shown in FIG. 18, in accordance with the invention.
Figure 20:
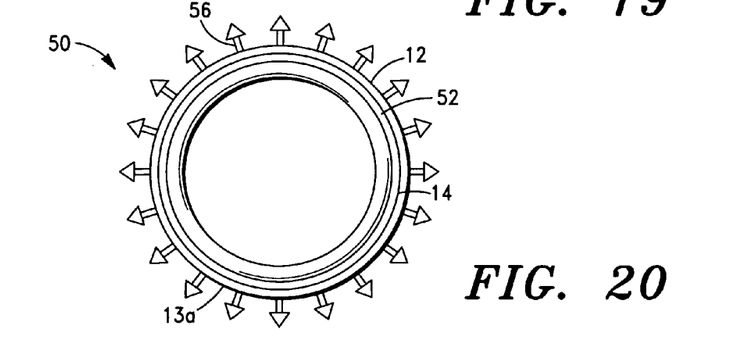
FIG. 20 is a front plan view of the ECM prosthesis shown in FIG. 18, in accordance with the invention.

Referring now to FIGS. 18-20, there is shown one embodiment of an ECM prosthesis 50 of the invention having a tubular ECM member 12, proximal and distal anchors 14, 16, and a microneedle member (or support scaffold) 52. As illustrated in FIG. 19, the support scaffold 52 includes a plurality of microneedles 56, which preferably extend through and project out of the ECM tubular member 12.

Figure 21:
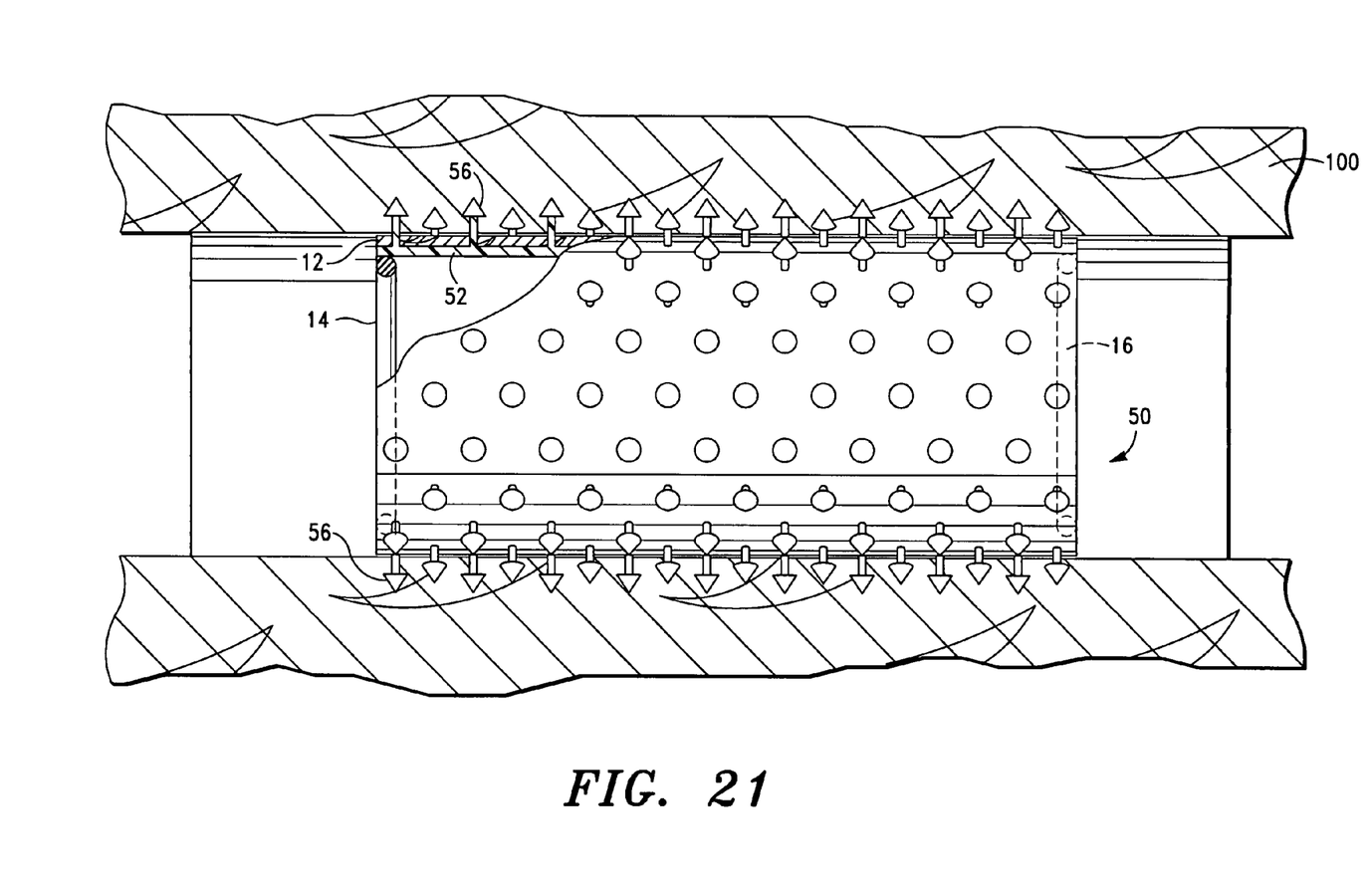
FIG. 21 is a side plan, sectional view of the ECM prosthesis shown in FIG. 18 in a post-deployment configuration in a cardiovascular vessel, in accordance with the invention.

As illustrated in FIG. 21, upon deployment of the prosthesis 50 in a body lumen or vessel, the anchors 14, 16 position and maintain the ends of the ECM member 12 proximate the vessel tissue (denoted "100"). The microneedles 56 also engage the vessel tissue 100 and secure the ECM member body proximate the vessel tissue 100.

In some embodiments of the invention, the ECM member includes at least one pharmacological agent or composition, which can comprise, without limitation, antibiotics or anti-fungal agents, anti-viral agents, anti-pain agents, anesthetics, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

Suitable pharmacological agents and/or compositions thus include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, Anti VGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

In some embodiments of the invention, the pharmacological agent specifically comprises an anti-inflammatory agent. According to the invention, suitable anti-inflammatory agents include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclopro-fen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium; indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

In some embodiments of the invention, the pharmacological composition comprises a statin. According to the invention, suitable statins include, without limitation, atorvastatin, cerivastatin, fluvastatin, lovastatin, mevastatin, pitavastatin, pravastatin, rosuvastatin, and simvastatin.

As discussed in detail above, the noted statins enhance the cell function, migration, angiogenesis, and decrease inflammation.

As also stated above, upon deployment of a prosthesis of the invention within a vessel, the ECM member, i.e. material, covers the target intima surface of the vessel, e.g., damaged or diseased region of the vessel, and provides a smooth, non-thrombogenic surface. The ECM material will also induce host tissue proliferation, bioremodeling, including neovascularization, e.g., vasculogenesis, angiogenesis, and intussusception, and regeneration of tissue structures with site-specific structural and functional properties.

In some embodiments of the invention, wherein the ECM member includes a pharmacological agent or a microneedle anchoring member having drug-eluting microneedles is employed, a desired biological and/or therapeutic action is also effectuated.

As will readily be appreciated by one having ordinary skill in the art, the present invention provides numerous advantages compared to prior art vascular endografts. Among the advantages are the following:

The provision of vascular prostheses that substantially reduce or eliminate (i) intimal hyperplasia after intervention in a vessel, (ii) the harsh biological responses associated with conventional polymeric and metal prostheses, and (iii) the formation of biofilm, inflammation and infection.

The provision of vascular prostheses that induce host tissue proliferation, bioremodeling and regeneration of new tissue and tissue structures with site-specific structural and functional properties.

The provision of vascular prostheses that administer a pharmacological agent and, thereby produce a desired biological and/or therapeutic effect.

The provision of vascular prostheses that include unique anchor members that temporarily position the ECM members proximate target tissue for a pre-determined period of time within the process of tissue growth, and have controlled degradation characteristics.

As will also readily be appreciated by one having ordinary skill in the art, the ECM prostheses can be readily employed in various medical procedures. The medical procedures include, without limitation, the treatment of coronary and peripheral vascular disease (PVD) in cardiovascular vessels, including, but not limited to, iliacs, superficial femoral artery, renal artery, tibial, popliteal, etc., deep vein thromboses (DVT), vascular bypasses, and coronary vascular repair.

It is understood that the noted applications of the ECM prostheses are merely exemplary and, thus, do not limit the scope of the possible applications and, hence, invention.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. An implantable extracellular matrix (ECM) vascular prosthesis, comprising:

an expandable tubular ECM member comprising a remodelable ECM material from a mammalian tissue source, said ECM member further comprising an interior and exterior surface, and proximal and distal ends, said interior surface defining a conduit through said ECM member, said conduit providing unrestricted fluid flow through said ECM member, said ECM member being capable of transitioning from a tubular member pre-deployment configuration, wherein said ECM member is capable of being positioned at a target position within a cardiovascular vessel, said cardiovascular vessel comprising host cardiovascular tissue having a first tissue temperature, to a tubular member post-deployment configuration, wherein at least a portion of said ECM member exterior surface is disposed proximate said host cardiovascular tissue of said cardiovascular vessel, said ECM member further comprising first and second expandable biocompatible anchors, said first expandable anchor being secured on said ECM member proximal end and proximate said ECM member interior surface, said second expandable anchor being secured on said ECM member distal end and proximate said ECM member interior surface, said first and second anchors being capable of transitioning from an anchor pre-deployment configuration at a first anchor temperature, wherein said ECM member is configured in said ECM member pre-deployment configuration, to an anchor post-deployment configuration when said ECM member is disposed in said cardiovascular vessel and subjected to said host cardiovascular tissue temperature, wherein said ECM member is configured in said ECM member post-deployment configuration and, wherein said first and second anchors position said ECM member exterior surface at said proximal and distal ends adjacent said host cardiovascular tissue of said cardiovascular vessel and maintain contact of said ECM member exterior surface at said proximal and distal ends to said host cardiovascular tissue of said cardiovascular tissue for a first temporary anchor support period of time.

2. The ECM vascular prosthesis of claim 1, wherein said mammalian tissue source is selected from the group consisting of the small intestine, large intestine, stomach, lung, liver, kidney, pancreas, placenta, heart, bladder, prostate, tissue surrounding growing enamel, tissue surrounding growing bone, and fetal tissue from a mammalian organ.

3. The ECM vascular prosthesis of claim 1, wherein said ECM member include one layer of said ECM material.

4. The ECM vascular prosthesis of claim 1, wherein said ECM member includes multiple layers of said ECM material.

5. The ECM vascular prosthesis of claim 1, wherein said first temporary anchor support period of time is within the process of cardiovascular tissue regeneration.

6. The ECM vascular prosthesis of claim 5, wherein said first temporary anchor support period of time is within the range of 12-36 months.

7. The ECM vascular prosthesis of claim 5, wherein said first temporary anchor support period of time is within the range of 3-12 months.

8. The ECM vascular prosthesis of claim 5, wherein said first temporary anchor support period of time is within the range of 1-3 months.

9. The ECM vascular prosthesis of claim 1, wherein said first and second anchors comprise a biocompatible shape memory alloy.

10. The ECM vascular prosthesis of claim 9, wherein said biocompatible shape memory alloy comprises Nitinol®.

11. The ECM vascular prosthesis of claim 1, wherein said first and second anchors comprise a single anchor ring.

12. The ECM vascular prosthesis of claim 1, wherein said first and second anchors exert a supporting force on said ECM member proximal and distal ends in the range of approximately 0.5-2.0 atm when said first and second anchors are in said post-deployment configuration.

13. The ECM vascular prosthesis of claim 12, wherein said supporting force diminishes to approximately 0 after said first temporary anchor support period of time.

* * * * *